United States Patent
Zheng et al.

(10) Patent No.: US 12,194,220 B2
(45) Date of Patent: Jan. 14, 2025

(54) HIGH ANTICOAGULATION ECMO AND EXTRACORPOREAL CIRCULATION CONSUMABLE

(71) Applicant: Wenzhou Safety (Emergency) Research Institute, Tianjin University, Wenzhou (CN)

(72) Inventors: Bin Zheng, Wenzhou (CN); Haojun Fan, Wenzhou (CN); Bowen Li, Wenzhou (CN); Tingting Hua, Wenzhou (CN)

(73) Assignee: Wenzhou Safety (Emergency) Research Institute, Tianjin University, Wenzhou (CN)

( * ) Notice: Subject to any disclaimer, the term of this patent is extended or adjusted under 35 U.S.C. 154(b) by 153 days.

(21) Appl. No.: 17/948,698

(22) Filed: Sep. 20, 2022

(65) Prior Publication Data

US 2024/0066201 A1  Feb. 29, 2024

(30) Foreign Application Priority Data

Aug. 24, 2022 (CN) .......................... 202211016979.2

(51) Int. Cl.

| A61M 1/36 | (2006.01) |
| A61L 31/02 | (2006.01) |
| A61L 31/04 | (2006.01) |
| A61L 31/06 | (2006.01) |
| A61L 33/00 | (2006.01) |
| A61L 33/02 | (2006.01) |
| A61L 33/06 | (2006.01) |

(Continued)

(52) U.S. Cl.
CPC ......... *A61M 1/3673* (2014.02); *A61L 31/028* (2013.01); *A61L 31/042* (2013.01); *A61L 31/047* (2013.01); *A61L 31/06* (2013.01); *A61L 33/0082* (2013.01); *A61L 33/027* (2013.01); *A61L 33/068* (2013.01); *A61L 33/08* (2013.01); *A61L 33/128* (2013.01); *A61M 1/3666* (2013.01); *A61L 2300/112* (2013.01); *A61L 2300/236* (2013.01); *A61L 2300/42* (2013.01); *A61L 2400/18* (2013.01); *A61M 2207/00* (2013.01)

(58) Field of Classification Search
CPC .................................................. A61M 1/3673
See application file for complete search history.

(56) References Cited

U.S. PATENT DOCUMENTS

2009/0287072 A1* 11/2009 Meyerhoff .............. A61L 27/54
523/112

FOREIGN PATENT DOCUMENTS

| CN | 209451036 U | 10/2019 |
| CN | 213374613 U | 6/2021 |

(Continued)

*Primary Examiner* — Dah-Wei D. Yuan
*Assistant Examiner* — Andrew J Bowman

(57) ABSTRACT

Disclosed is a high anticoagulation ECMO and extracorporeal circulation consumable, which include the following preparation methods: S1, aminating the surface of ECMO blood circulation device and extracorporeal circulation consumables; S2, activating heparin groups; S3, heparinizing the ECMO blood circulation device and extracorporeal circulation consumables; S4, modification of enhancer. The application can produce a novel high anticoagulation extracorporeal circulation tube with low price and high biocompatibility, which expands the application in clinic.

10 Claims, 4 Drawing Sheets

(51) Int. Cl.
*A61L 33/08* (2006.01)
*A61L 33/12* (2006.01)

(56) References Cited

FOREIGN PATENT DOCUMENTS

| CN | 213698242 U | 7/2021 |
| CN | 214911391 U | 11/2021 |

* cited by examiner

HIGH ANTICOAGULATION ECMO AND EXTRACORPOREAL CIRCULATION CONSUMABLE

CROSS-REFERENCE TO RELATED APPLICATIONS

The application claims priority to Chinese patent application No. 202211016979.2, filed on Aug. 24, 2022, the entire contents of which are incorporated herein by reference.

TECHNICAL FIELD

The application relates to the technical field of hemodialysis circulation tube, in particular to a high anticoagulation ECMO and extracorporeal circulation consumable.

BACKGROUND

At present, the development of cardiac surgery drives the research and application of biomedical materials. Cardiopulmonary bypass, dialysis and hemofiltration urgently need the development and application of related biomedical materials. The application of biomaterials faces two major problems: biocompatibility and blood compatibility. Biological materials in contact with blood will stimulate the host defense mechanism, especially the blood stabilization mechanism, which will cascade and cause thrombosis and embolism, which will seriously endanger the patient's life. It is necessary to develop a high anticoagulation ECMO and extracorporeal circulation consumable.

However, at present, there are some consumables for extracorporeal circulation with heparinized coating, which have poor anticoagulation effect due to the easy shedding of anticoagulations. Therefore, a kind of high anticoagulation ECMO and extracorporeal circulation consumable is urgently needed.

SUMMARY

The present application provides a high anticoagulation ECMO and extracorporeal circulation consumable to solve the problems mentioned in the background technology.

To achieve the above objective, the present application adopts the following technical scheme:

A high anticoagulation ECMO and extracorporeal circulation consumable, including the following preparation methods:

S1, aminating the surface of ECMO blood circulation device and extracorporeal circulation consumables: adding raw materials rich in amino functional groups into organic solvent, fully stirring and mixing, pouring into the ECMO blood circulation device and extracorporeal circulation consumables, refluxing at 20-80° C. for 2-10 hours, grafting the raw materials rich in amino functional groups onto the inner wall contacting with blood, so that a large amount of amino groups are loaded on the surface, and washing to obtain amino-modified ECMO blood circulation device and extracorporeal circulation consumables;

S2, activating heparin groups: activating heparin groups by direct coupling method, dissolving heparin sodium in IVIES buffer, adding EDC and NHS, and stirring the solution in ice-water bath for 1 h-5 h to activate active groups of the heparin and generate heparin containing active carboxyl groups;

S3, heparinizing the ECMO blood circulation device and extracorporeal circulation consumables: adding heparin-activated mixed solution into the amino-modified ECMO blood circulation device and extracorporeal circulation consumables, refluxing for 1-20 hours, discharging the solution, repeating this step for 1-3 times, washing with a mixed solution of ethanol and distilled water to obtain heparinized ECMO blood circulation device and extracorporeal circulation consumables, and drying for later use;

S4, modification of enhancer: after the heparinization of the ECMO blood circulation device and extracorporeal circulation consumables is completed, using albumin, functionalized PEG which can react with amino groups, and phosphate to further surface modify the heparinized ECMO blood circulation device and extracorporeal circulation consumables to block the sites not modified by heparinization, so as to shield the adsorption of platelets and protein in blood on the inner wall.

As a further improvement scheme of the technical scheme, in S1, after the reaction, characterizing the grafting effect by FT-IR and water contact angle measurement, and observing whether the rich in amino functional groups appears in the FT-IR spectrum and the water contact angle decreases.

As a further improvement scheme of the technical scheme, in S2, concentration of the heparin sodium is $1 \times 10^0 \sim 1 \times 10^6$ ug/milliliter (ml.), pH of the MES is 4.0~7.0, and the concentration of EDC and NHS is $1 \times 10^0$ ug/ml~$1 \times 10^4$ ug/ml.

As a further improvement scheme of the technical scheme, in S3, when the mixed solution of ethanol and distilled water is used for washing, the volume ratio of ethanol to distilled water is 0%-100%, so as to efficiently clean unreacted monomers or possible residual harmful components in the ECMO blood circulation device and extracorporeal circulation consumables.

As a further improvement scheme of the technical scheme, in S4, using a plurality of anticoagulation methods to further surface modify the heparinized ECMO blood circulation device and extracorporeal circulation consumables, including albumin modification, functionalized PEG modification and phosphate modification, and the concentration of the modified raw materials is $1 \times 10^0 \sim 1 \times 10^6$ ug/ml.

As a further improvement scheme of the technical scheme, the albumin modification is to modify the surface of the heparinized ECMO blood circulation device and extracorporeal circulation consumables with an enhancer containing albumin, so as to effectively reduce thrombosis on the surface of the heparinized ECMO blood circulation device and extracorporeal circulation consumables.

As a further improvement scheme of the technical scheme, the functionalized PEG includes any one or more of active carboxylated PEG, PEG containing succinimide ester, PEG containing isothiocyanine group and PEG containing sulfonyl chloride group, using the functionalized PEG to modify the surface of the heparinized ECMO blood circulation device and extracorporeal circulation consumables to reduce the interaction between the surface of the heparinized ECMO blood circulation device and extracorporeal circulation consumables and blood components.

As a further improvement scheme of the technical scheme, the phosphate modification is to modify the surface of the heparinized ECMO blood circulation device and extracorporeal circulation consumables with a phosphate-containing reinforcing agent, so as to effectively reduce the adsorption of platelets and protein on the surface of the heparinized ECMO blood circulation device and extracorporeal circulation consumables.

As a further improvement scheme of the technical scheme, in S1, the organic solvent includes any one or more of chloroform, carbon tetrachloride, dichloromethane, dichloroethane, benzene, toluene or xylene.

As a further improvement scheme of the technical scheme, in S1, the raw materials rich in amino functional groups include any one or more of PEI, chitosan, polylysine, ethylenediamine, urea-formaldehyde, aniline and amino-terminated hyperbranched polyamide.

Compared with the prior art, the present application has the advantages that:

Firstly, organic solvents such as chloroform, carbon tetrachloride, dichloromethane, dichloroethane, benzene, toluene and xylene, and raw materials rich in amino functional groups such as PEI, chitosan, polylysine, ethylenediamine, urea-formaldehyde, melamine, aniline and amino-terminated hyperbranched polyamide are mixed and added into PVC/PC tube, so that the surface is loaded with a large amount of amino groups. Then EDC/NHS is used to catalyze heparin to generate heparin containing carboxyl groups, and heparin is covalently bonded to the inner surface of the PVC/PC tube through the reaction of carboxyl groups on heparin molecules and amino groups on the inner surface of the PVC/PC tube, so that heparinization is more stable. After that, anticoagulation enhancer is used to modify the tube, and finally the anticoagulation effect of the PVC/PC tube as ECMO blood circulation tube is significantly improved, and the usable time is at least half a month. The present application can produce a novel high anticoagulation extracorporeal circulation tube with low price and high biocompatibility, which expands the wide application in clinic, fills up the research gap in related fields.

The above description is only a summary of the technical scheme of the present application. In order to understand the technical means of the present application more clearly and implement it according to the contents of the description, the following detailed description will be given with the preferred embodiment of the present application and the accompanying drawings. The specific embodiments of the present application are given in detail by the following examples and their drawings.

BRIEF DESCRIPTION OF THE DRAWINGS

The drawings illustrated here are used to provide a further understanding of the present application and form a part of this application. The illustrative embodiments of the present application and their descriptions are used to explain the present application, and do not constitute undue limitations on the present application. In the attached drawings.

DETAILED DESCRIPTION OF THE EMBODIMENTS

The principles and features of the present application will be described with reference to the accompanying drawings. Examples are only used to explain the present application, but not to limit the scope of the present application. In the following paragraphs, the present application will be more specifically described by way of example with reference to the accompanying drawings. The advantages and features of the present application will be more apparent from the following description and claims. It should be noted that the drawings are all in a very simplified form and in inaccurate proportions, and are only used to facilitate and clearly explain the purpose of the embodiments of the present application.

Unless otherwise defined, all technical and scientific terms used herein have the same meanings as commonly understood by those skilled in the technical field of the present application. The terminology used in this specification of the present application is only for the purpose of describing specific embodiments, and is not intended to limit the present application. As used herein, the term "and/or" includes any and all combinations of one or more related listed items.

Figure 1:
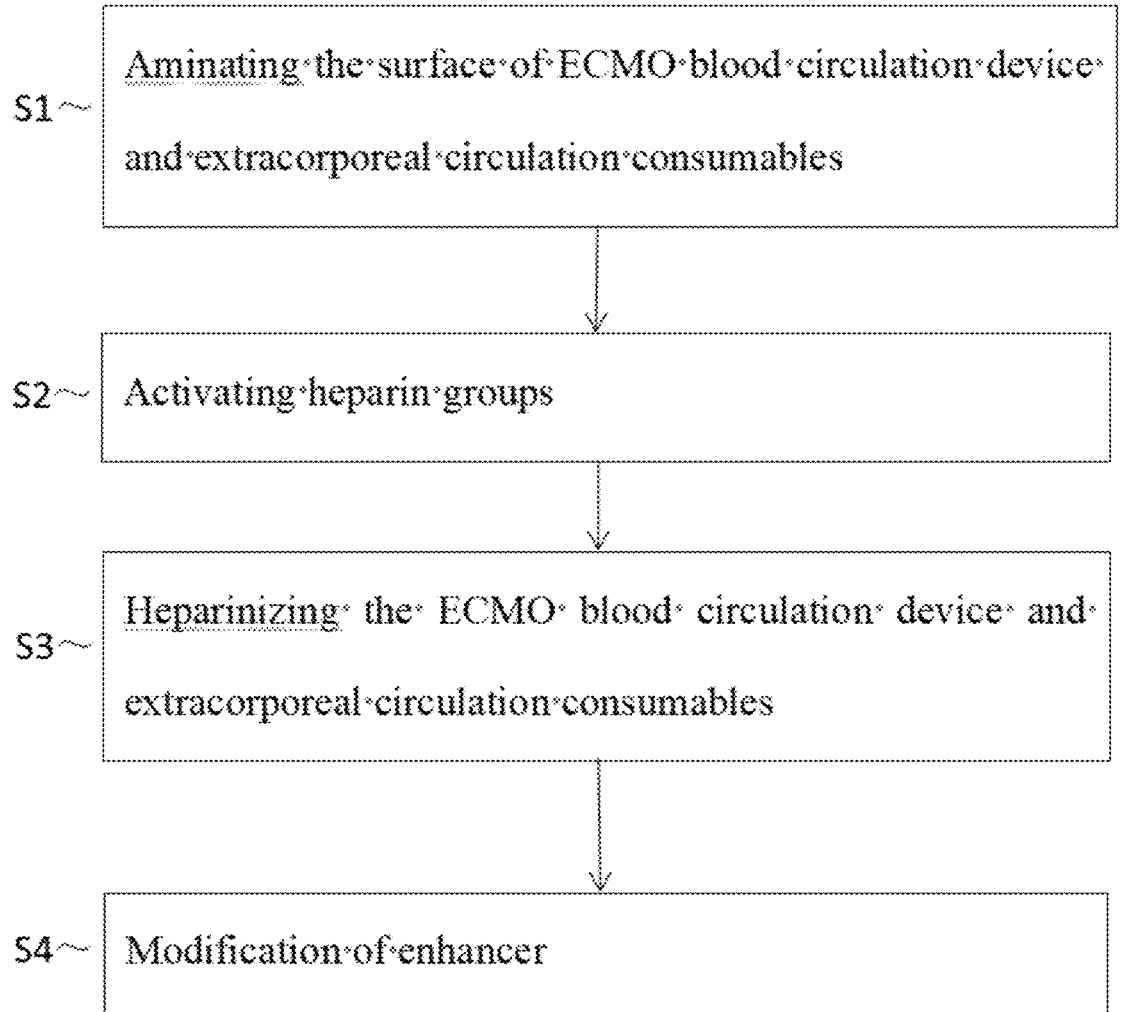
FIG. 1 is a schematic diagram of a preparation method of a high anticoagulation ECMO and extracorporeal circulation consumable proposed by the present application.
Figure 2:
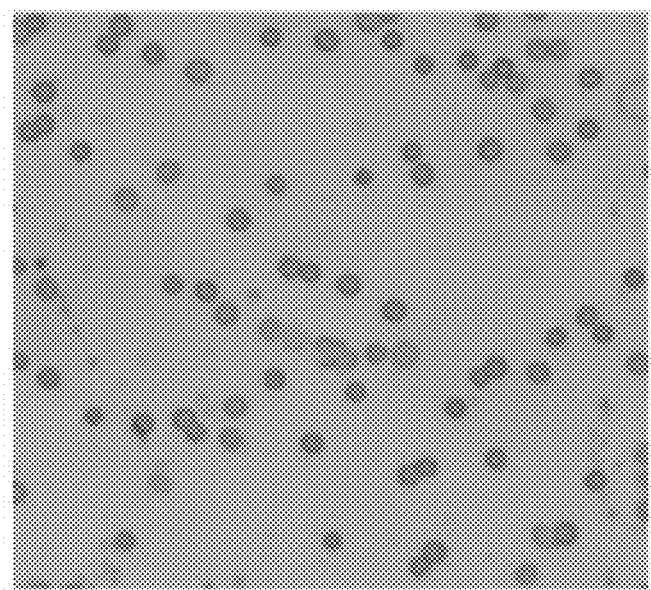
FIG. 2 is the distribution of heparin on the surface of high anticoagulation ECMO and extracorporeal circulation consumable before erythrocyte agglutination test.

Please refer to FIG. 1 and FIG. 2. In the embodiment of the application, a high anticoagulation ECMO and extracorporeal circulation consumable includes the following preparation methods:

S1, aminating the surface of ECMO blood circulation device and extracorporeal circulation consumables: adding raw materials rich in amino functional groups (such as PEI, chitosan, polylysine, ethylenediamine, urea-formaldehyde, melamine, aniline and amino-terminated hyperbranched polyamide) into organic solvent (such as chloroform, carbon tetrachloride, dichloromethane, dichloroethane, benzene, toluene and xylene), fully stirring and mixing, pouring into the ECMO blood circulation device and extracorporeal circulation consumables, refluxing at 20-80° C. for 2-10 hours, grafting the raw materials rich in amino functional groups onto the inner wall contacting with blood, so that a large amount of amino groups are loaded on the surface, and washing to obtain amino-modified ECMO blood circulation device and extracorporeal circulation consumables. After the reaction, characterizing the grafting effect by FT-IR and water contact angle measurement, and observing whether the rich in amino functional groups appears in the FT-IR spectrum and the water contact angle decreases;

S2, activating heparin groups: activating heparin groups by direct coupling method, dissolving heparin sodium in IVIES buffer with pH of 4.0-7.0, adding EDC and NHS, and stirring the solution in ice-water bath for 1 h-5 h to activate active groups of the heparin and generate heparin containing active carboxyl groups;

S3, heparinizing the ECMO blood circulation device and extracorporeal circulation consumables: adding heparin-activated mixed solution into the amino-modified ECMO blood circulation device and extracorporeal circulation consumables, refluxing for 1-20 hours, discharging the solution, repeating this step for 1-3 times, washing with a mixed solution of ethanol and distilled water to obtain heparinized ECMO blood circulation device and extracorporeal circulation consumables, and drying for later use;

S4, modification of enhancer: after the heparinization of the ECMO blood circulation device and extracorporeal circulation consumables is completed, using albumin, functionalized PEG which can react with amino groups, and phosphate to further surface modify the heparinized ECMO blood circulation device and extracorporeal circulation consumables to block the sites not modified by heparinization, so as to shield the adsorption of platelets and protein in blood on the inner wall. Various anticoagulation methods are used to further surface modify the heparinized ECMO blood circulation device and extracorporeal circulation consumables, including albumin modification, functionalized PEG modification and phosphate modification, and the concentration of modification raw materials is $1\times10^0$ ug/ml~$1\times10^6$ ug/ml.

Specifically, the albumin modification is to modify the surface of the heparinized ECMO blood circulation device and extracorporeal circulation consumables with an enhancer containing albumin, which is used to effectively reduce thrombosis on the surface of heparinized ECMO blood circulation device and extracorporeal circulation consumables.

Specifically, the functionalized PEG includes any one or more of active carboxylated PEG, PEG containing succinimide ester, PEG containing isothiocyanine group and PEG containing sulfonyl chloride group. The functionalized PEG is used to modify the surface of the heparinized ECMO blood circulation device and extracorporeal circulation consumables, so as to reduce the interaction between the surface of the heparinized ECMO blood circulation device and extracorporeal circulation consumables and blood components.

Specifically, the phosphate modification is to modify the surface of the heparinized ECMO blood circulation device and extracorporeal circulation consumables with a phosphate-containing reinforcing agent, so as to effectively reduce the adsorption of platelets and protein on the surface of the heparinized ECMO blood circulation device and extracorporeal circulation consumables.

The working principle of the present application is:

Firstly, organic solvents such as chloroform, carbon tetrachloride, dichloromethane, dichloroethane, benzene, toluene and xylene, and raw materials rich in amino functional groups such as PEI, chitosan, polylysine, ethylenediamine, urea-formaldehyde, melamine, aniline and amino-terminated hyperbranched polyamide are mixed and added into PVC/PC tube, so that the surface is loaded with a large amount of amino groups. Then EDC/NHS is used to catalyze heparin to generate heparin containing carboxyl groups, and heparin is covalently bonded to the inner surface of the PVC/PC tube through the reaction of carboxyl groups on heparin molecules and amino groups on the inner surface of the PVC/PC tube, so that heparinization is more stable. After that, anticoagulation enhancer is used to modify the tube, and finally the anticoagulation effect of the PVC/PC tube as ECMO blood circulation tube is significantly improved, and the usable time is at least half a month. The present application proved the blood compatibility and cell safety of ECMO blood circulation tube. The present application proves that the ECMO blood circulation tube has blood compatibility and cell safety.

FIG. 2 is the distribution of heparin on the surface of high anticoagulation ECMO and extracorporeal circulation consumable before erythrocyte agglutination test.

Figure 3:
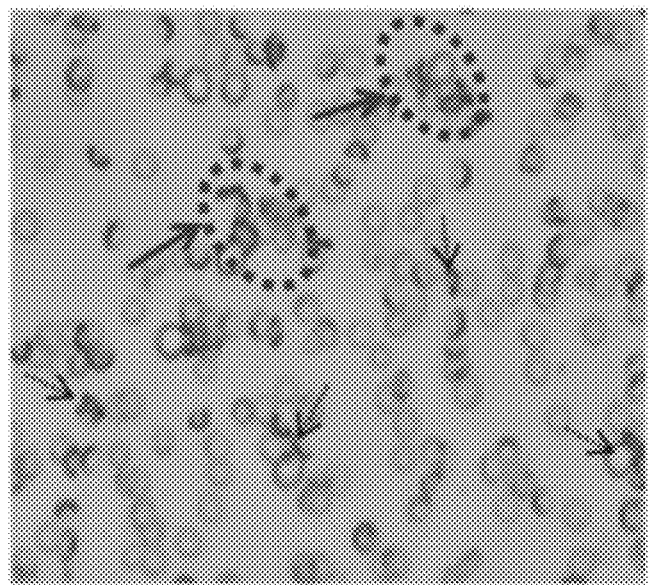
FIG. 3 is the result of erythrocyte agglutination test of heparin-free extracorporeal circulation consumable.
Figure 4:
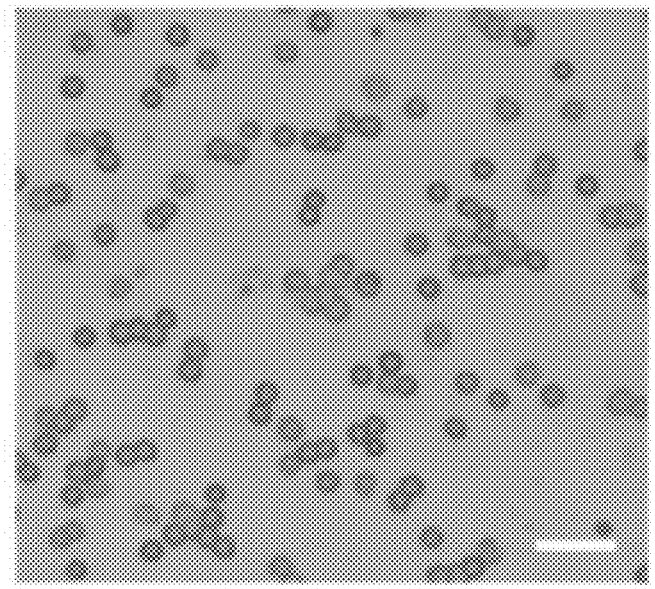
FIG. 4 is the result of erythrocyte agglutination test of heparinized extracorporeal circulation consumable.

FIG. 3 is the result of erythrocyte agglutination test of heparin-free extracorporeal circulation consumable. FIG. 4 is the result of erythrocyte agglutination test of heparinized extracorporeal circulation consumable. It can be clearly seen that there is no erythrocyte agglutination on the surface of heparinized extracorporeal circulation consumable.

The above description is only a preferred embodiment of the present application, and does not limit the present application in any form. Those of ordinary skill in the industry can smoothly implement the application as shown in the drawings and described above; However, those skilled in the art who make some changes, modifications and equivalent changes by using the technical contents disclosed above without departing from the scope of the technical scheme of the present application are equivalent embodiments of the present application. Meanwhile, any changes, modifications and evolutions equivalent to the above embodiments made according to the essential technology of the present application are still within the protection scope of the technical scheme of the present application.

What is claimed is:

1. A high anticoagulation extracorporeal membrane oxygenation (ECMO) device and extracorporeal circulation consumables, comprising the following preparation methods:

S1, aminating a surface of the ECMO device and extracorporeal circulation consumables: adding raw materials containing amino functional groups into an organic solvent to obtain a first mixture solution, stirring and mixing the first mixture solution, pouring the first mixture solution into the ECMO device and extracorporeal circulation consumables, refluxing at a temperature ranging from 20° C. to 80° C. for 2 to 10 hours, to graft the raw materials containing amino functional groups onto an inner wall of the ECMO device and extracorporeal circulation consumables contacting with blood, so that the inner wall are loaded with amino functional groups, and washing to obtain amino-modified ECMO device and extracorporeal circulation consumables;

S2, activating heparin groups by direct coupling method: dissolving heparin sodium in 2-(N-morpholino)ethanesulfonic acid (MES) buffer to obtain a heparin solution, adding 1-Ethyl-3-(3-dimethylaminopropyl)carbodimide(EDC) and N-Hydroxysuccinimide (NHS) to the heparin solution to obtain a second mixture solution, and stirring the second mixture solution in an ice-water bath for 1 to 5 hours to activate active groups of heparin and generate an activated heparin solution containing active carboxyl groups;

S3, heparinizing the amino-modified ECMO device and extracorporeal circulation consumables: adding the activated heparin solution into the amino-modified ECMO device and extracorporeal circulation consumables, refluxing for 1 to 20 hours and discharging the activated heparin solution, washing the amino-modified ECMO device and extracorporeal circulation consumables with a mixed solution of ethanol and distilled water to obtain a heparinized ECMO device and extracorporeal circulation consumables;

S4, modifying the heparinized ECMO device and extracorporeal circulation consumables with enhances: modifying a surface of the heparinized ECMO device and extracorporeal circulation consumables with albumin, functionalized polyethylene glycol (PEG) which can react with amino groups, and phosphate to block sites on the heparinized ECMO device and extracorporeal circulation consumables not modified by heparinization process, to shield adsorption of platelets and protein in blood on the inner wall.

2. The high anticoagulation ECMO device and extracorporeal circulation consumables according to claim 1, wherein in step S1, characterizing a grafting effect by Fourier Transform Infrared Spectroscopy (FT-IR) and water contact angle measurement, and observing whether the amino functional groups appears in a FT-IR spectrum and the water contact angle decreases.

3. The high anticoagulation ECMO device and extracorporeal circulation consumables according to claim 1, wherein in step S2, a concentration of the heparin sodium ranges from $1\times10^0$ ug/ml to $1\times10^6$ ug/ml, a pH of the MES buffer ranges from 4.0 to 7.0, and a concentration of EDC and NHS range from $1\times10^0$ ug/ml to $1\times10^4$ ug/ml.

4. The high anticoagulation ECMO device and extracorporeal circulation consumables according to claim 1, wherein in step S3, a volume ratio of ethanol to distilled water is 0%-100%, to clean unreacted monomers or possible residual harmful components in the ECMO device and extracorporeal circulation consumables.

5. The high anticoagulation ECMO device and extracorporeal circulation consumables according to claim 1, wherein in step S4, using a plurality of anticoagulation methods to surface modify the heparinized ECMO device and extracorporeal circulation consumables, the anticoagulation methods comprises albumin modification, functionalized PEG modification and phosphate modification, and a concentration of the albumin, PEG and phosphate ranges from $1\times10^0$ to $1\times10^6$ ug/ml.

6. The high anticoagulation ECMO device and extracorporeal circulation consumables according to claim 5, wherein the albumin modification is to modify the surface of the heparinized ECMO device and extracorporeal circulation consumables with an enhancer containing albumin, so as to reduce thrombosis on the surface of the heparinized ECMO device and extracorporeal circulation consumables.

7. The high anticoagulation ECMO device and extracorporeal circulation consumables according to claim 5, wherein the functionalized PEG comprises at least one of active carboxylated PEG, PEG containing succinimide ester, PEG containing isothiocyanine group, or PEG containing sulfonyl chloride group; the functionalized PEG is used to reduce interactions between the surface of the heparinized ECMO device and extracorporeal circulation consumables and blood components.

8. The high anticoagulation ECMO device and extracorporeal circulation consumables according to claim 5, wherein the phosphate modification is to modify the surface of the heparinized ECMO device and extracorporeal circulation consumables with a phosphate-containing reinforcing agent, so as to reduce a adsorption of platelets and protein on the surface of the heparinized ECMO device and extracorporeal circulation consumables.

9. The high anticoagulation ECMO device and extracorporeal circulation consumables according to claim 1, wherein in step S1, the organic solvent comprises at least one of chloroform, carbon tetrachloride, dichloromethane, dichloroethane, benzene, or toluene or xylene.

10. The high anticoagulation ECMO device and extracorporeal circulation consumables according to claim 1, wherein in step S1, the raw materials containing amino functional groups comprise at least one of PEI, chitosan, polylysine, ethylenediamine, urea-formaldehyde, aniline, or amino-terminated hyperbranched polyamide.

* * * * *